(12) United States Patent
Lee et al.

(10) Patent No.: US 9,469,728 B2
(45) Date of Patent: *Oct. 18, 2016

(54) TEMPERATURE AND PH-SENSITIVE BLOCK COPOLYMER HAVING EXCELLENT SAFTY IN VIVO AND HYDROGEL AND DRUG DELIVERY SYSTEM USING THEREOF

(75) Inventors: Doo Sung Lee, Suwon-si (KR); Minh Khanh Nguyen, Suwon-si (KR); Bong Sup Kim, Suwon-si (KR)

(73) Assignee: SUNGKYUNKWAN UNIVERSITY FOUNDATION FOR CORPORATE, Suwon-si (KR)

( * ) Notice: Subject to any disclaimer, the term of this patent is extended or adjusted under 35 U.S.C. 154(b) by 1175 days.

This patent is subject to a terminal disclaimer.

(21) Appl. No.: 12/676,828

(22) PCT Filed: Sep. 5, 2008

(86) PCT No.: PCT/KR2008/005270
§ 371 (c)(1),
(2), (4) Date: Mar. 5, 2010

(87) PCT Pub. No.: WO2009/031861
PCT Pub. Date: Mar. 12, 2009

(65) Prior Publication Data
US 2010/0233264 A1    Sep. 16, 2010

(30) Foreign Application Priority Data
Sep. 6, 2007    (KR) .................. 10-2007-0090625

(51) Int. Cl.
| | |
|---|---|
| A61K 9/00 | (2006.01) |
| A61K 47/34 | (2006.01) |
| C08G 65/30 | (2006.01) |
| C08G 65/332 | (2006.01) |
| C08G 65/333 | (2006.01) |

(52) U.S. Cl.
CPC ............ *C08G 65/30* (2013.01); *A61K 9/0024* (2013.01); *A61K 47/34* (2013.01); *C08G 65/3322* (2013.01); *C08G 65/33317* (2013.01); *C08G 65/33324* (2013.01); *C08L 2203/02* (2013.01); *C08L 2205/05* (2013.01)

(58) Field of Classification Search
None
See application file for complete search history.

(56) References Cited

U.S. PATENT DOCUMENTS

| | | | |
|---|---|---|---|
| 4,942,035 A | 7/1990 | Churchhill et al. | |
| 5,476,909 A | 12/1995 | Kim et al. | |
| 6,476,156 B1 | 11/2002 | Kim et al. | |
| 7,160,971 B2 | 1/2007 | Mallapragada et al. | |
| 2002/0131951 A1* | 9/2002 | Langer et al. | 424/78.37 |
| 2003/0147958 A1 | 8/2003 | Ahn et al. | |
| 2004/0151690 A1 | 8/2004 | Nakanishi et al. | |
| 2007/0059271 A1 | 3/2007 | Kataoka et al. | |

FOREIGN PATENT DOCUMENTS

| | | |
|---|---|---|
| KR | 10-2005-0047763 A | 5/2005 |
| WO | 2006/098547 A1 | 9/2006 |
| WO | 2006/109945 A1 | 10/2006 |

OTHER PUBLICATIONS

Kissel, T., et al., "ABA-triblock copolymers from biodegradable polyester A-blocks and hydrophilic poly(ethylene oxide) B-blocks as a candidate for in situ forming hydrogel delivery systems for proteins", 2002, Advanced Drug Delivery Reviews, 54, pp. 99-134.*
Kim, M.S., et al. "pH-Responsive Peg-Poly(b-amino ester) Block Copolymer Micelles with a Sharp Transition", 2006, Macromolecular Rapid Communications, 27, pp. 447-452.*
Kim, T., et al., "PAMAM-PEG-PAMAM: Novel Triblock Copolymer as a Biocompatible and Efficient Gene Delivery Carrier", Biomacromolecules, 2004, pp. 2487-2492.*

* cited by examiner

*Primary Examiner* — Michael G Hartley
*Assistant Examiner* — Lance Rider
(74) *Attorney, Agent, or Firm* — Sughrue Mion, PLLC

(57) ABSTRACT

Disclosed herein are pH- and temperature-sensitive block copolymer with excellent safety and a method for preparing the same and a hydrogel and a drug carrier using the block copolymer. According to the present invention, the pH- and temperature-sensitive block copolymer comprises: obtained by copolymerization of: (a) polyethylene glycol-based compound (A); and (b) poly (β-amino ester)-based oligomer (B) or poly (amido amine)-based oligomer (C) or coupling of mixture (D) thereof. In order to control biodegradation rate, the block copolymer is mixed with poly (amido amine)-based oligomer instead of the poly (β-amino ester)-based oligomer and then coupling them.

8 Claims, 3 Drawing Sheets

TEMPERATURE AND PH-SENSITIVE BLOCK COPOLYMER HAVING EXCELLENT SAFTY IN VIVO AND HYDROGEL AND DRUG DELIVERY SYSTEM USING THEREOF

TECHNICAL FIELD

The present invention relates to a pH- and temperature-sensitive block copolymer hydrogel and a drug carrier employing the block copolymer. More particularly, the present invention relates to an injectable pH-sensitive block copolymer hydrogel with excellent safety and a drug carrier employing the same. The pH-sensitive block copolymer hydrogel according to the present invention is capable of sustained drug delivery depending on pH variations and temperature in the body in the absence with materials, which has biodegradability but accumulated in the body to produce various side effects. Additionally, the components of the pH-sensitive block copolymer hydrogel according to the present invention are biodegraded to be completely released outside body when injected in vivo and have controllable biodegradation rate in the body.

BACKGROUND ART

In the field of biocompatible polymers, polymers have been employed instead of various medical treatments and bodies. Recently, biodegradable polymers or amphiphilic polymers having both hydrophobicity and hydrophilicity have been of interest. Particularly, drug carriers changing molecular structure and controlling sol-gel transition phenomena by forming hydrogels using block copolymers employing the above-mentioned biodegradable polymers or amphiphilic polymers are actively conducted.

U.S. Pat. No. 4,942,035 discloses the problem that polyethylene glycol and polyethylene oxide-polypropylelen oxide-polyethyleneoxide block copolymer (usually called 'Pluronic' are not degraded in vivo using the copolymerization of polyalkylene glycol being hydrophilic polymer, polylactide or polyglycolide being biodegradable polyester polymer, and polycaprolactone.

And, U.S. Pat. No. 5,476,909 discloses a biodegradable triblock (A-B-A) copolymer. Hydrophobic blocks (A) are limited as polylactic acid (PLA), polyglycolic acid (PGA), or derivatives thereof. The hydrophilic block (B) is limited as polyethylene glycol (PEG) or derivatives thereof.

Meanwhile, Korean Patent No. 2006-0574341 discloses a pH-sensitive polymer comprising sulfonamide groups, and a preparation method thereof. This patent relates mainly to either a change in the solubility of linear polymers formed by the random copolymerization of sulfonamide monomers with DMAAm or NiPAAm, or the swelling index of cross-linked polymers thereof.

Additionally, Korean Patent No. 2006-0665672 discloses a pH- and temperature-sensitive block copolymer and hydrogels using the same and ionic complex with hydrogel drugs according to ionization and de-ionization of poly (β-amino ester) and poly (amido amine) depending on pH variations, and continuous drug ejection based on the above-mentioned phenomenon while undergoing copolymerization of temperature-sensitive and hydrophilic polymer polyalkylene-based compound, aliphatic polyester polymer being biodegradable polymer and hydrophobic polymer, and poly (β-amino ester) and poly (amido amine) being pH-sensitive polymer through a conventional reaction mechanism such as Michael reaction mechanism. In these multi-block copolymers, it is necessary to examine interaction and safety stability of block copolymer degraded in vivo and drugs.

The above-described prior arts were so designed that a sol-gel transition phenomenon is shown by the use of the block copolymer of the hydrophobic biodegradable polymer with the hydrophilic polymer. The block copolymer when injected in vivo in an aqueous solution form, a sol-state, is changed into a gel state. Thus, the block copolymer was used as a sustained drug delivery system which carries and slowly releases drugs in vivo. However, block copolymer that exhibits a temperature-sensitive sol-gel transition phenomenon cause problems, such as the clogging phenomenon of injection needles occurring during injection before in vivo injection, since in vivo temperature and the temperature of the injection needles are adjusted to the same temperature by thermal equilibrium. In addition, hydrophobic moieties comprised of PLA, PGA, PLGA, PCGA, PCL, or PCLA that are used as biodegradable polymer are reported to exhibit pH-sensitivity. Block copolymer using poly (β-amino ester) having pH-sensitivity is limitedly used as long-term sustained-drug delivery system. However, they are not suitable for practical use in the drug delivery system.

Moreover, in U.S. Pat. No. 6,476,156, there are two main problems. One is a coupling process of PEG, PLA, PGA, and PLC. The other is unsuitable practical use because pH variations in vivo are not considered.

DISCLOSURE

Technical Problem

The present invention has been made in an effort to solve the above problems, and it is an object of the present invention to provide a pH- and temperature-sensitive block copolymer and a method for preparing the same.

It is another object of the present invention is to provide a pH- and temperature-sensitive block copolymer comprised of only nontoxic materials and degraded into release outside body and a method for preparing the same.

It is still another object of the present invention is to provide a pH- and temperature-sensitive block copolymer capable of controlling biodegradation rate by controlling block copolymers and a method for preparing the same.

It is yet another object of the present invention is to provide a pH- and temperature-sensitive block copolymer with safety in vivo suppressing initial burst release phenomenon of a drug to be used as a hydrogel drug carrier and a method for preparing the same and a drug carrier using the block copolymer.

It is still yet another object of the present invention is to provide a hydrogel-type drug carrier having bioactive material be included in the block copolymer.

It is still yet another object of the present invention is to provide a pH- and temperature-sensitive block copolymer with safety in vivo designed to sustained for use in the field of cancel-cells, generic variations, and so forth by modifying the constitutional elements of the block copolymer, molar ratio, molecular weight of each constitutional element and/or functional groups therein and a method for preparing the same and a drug carrier using the block copolymer.

Technical Solution

Pursuant to embodiments of the present invention, a pH- and temperature-sensitive block copolymer with excellent human stability obtained by copolymerization of: (a) polyethylene glycol-based compound (A); and (b) poly (β-amino ester)-based oligomer (B) or poly (amido amine)-based oligomer (C) or coupling of mixture (D) thereof.

Pursuant to some embodiments of the present invention, (B-A-B) or (C-A-C) or (BC)-A-(BC) triblock copolymer is further included.

Pursuant to another embodiments of the present invention, (BC)-A-(BC) triblock is further included.

Pursuant to yet another embodiment of the present invention, the polyethylene glycol-based compound is represented by the following formula 1:

[Formula 1]

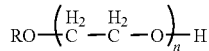

wherein R represents hydrogen or alkyl group containing 1 to 5 carbon atoms, and n is a natural number ranging from 11 to 45.

Pursuant to further embodiments of the present invention, the molecular weight of the polyethylene glycol-based compound is 500 to 8,000.

Pursuant to still further embodiments of the present invention, the molecular weight of the polyethylene glycol (PEG) where R in the formula 1 represents hydrogen is 1,000 to 6,000.

Pursuant to still further embodiments of the present invention, the molecular weight of the methoxy polyethylene glycol (MPEG) where R in the formula 1 represents methyl group is 1,000 to 7,000.

Pursuant to still further embodiments of the present invention, the poly (β-amino ester)-based precursor further includes at least one substituent selected from the group consisting of primary amine group, secondary amine group, and bisacrylate reacted with polyethylene glycol-based compound.

Pursuant to still further embodiments of the present invention, the poly (β-amino ester)-based oligomer further includes functional group of hydroxyl groups (—OH), carboxyl groups (—COOH), or amine groups (—NH$_2$).

Pursuant to still further embodiments of the present invention, the poly (β-amino ester)-based oligomer, the poly (amido amine)-based oligomer, or partial mixture thereof includes tertiary amine group ionized under pH 7.0.

Pursuant to still further embodiments of the present invention, the molecular weight of the poly (β-amino ester)-based oligomer or the poly (amido amine)-based oligomer is 1,000 to 5,000.

Pursuant to still further embodiments of the present invention, the molecular weight of the poly (β-amino ester)-based oligomer or the poly (amido amine)-based oligomer is 1,000 to 5,000.

Pursuant to still further embodiments of the present invention, the pH- and temperature-sensitive block copolymer which is represented by the following formula:

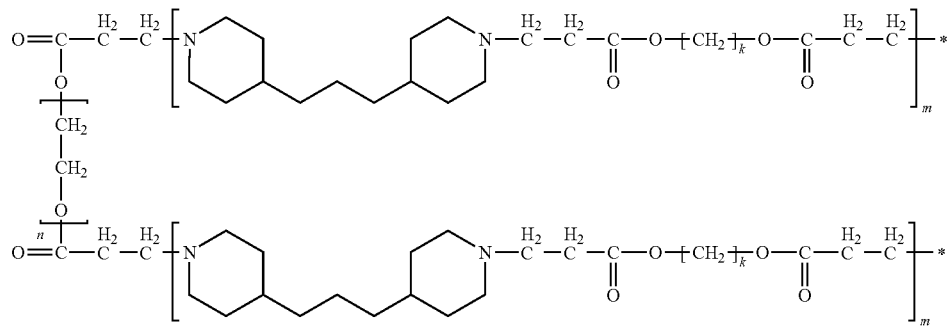

wherein k is a natural number ranging from 4 to 10, n is a natural number ranging from 11 to 45, and m is a natural number ranging from 10 to 100.

Pursuant to still further embodiments of the present invention, the molecular weight of the block copolymer is 3,000 to 32,000.

Pursuant to still further embodiments of the present invention, the molecular weight ratio of the polyethylene glycol-based compound (A) and the poly (β-amino ester)-based oligomer (B) is 1:1-4.

Pursuant to still further embodiments of the present invention, the block copolymer forms hydrogel at pH 7.0 to 7.4 and sol-sate pH 3.0 to under 7.0.

Pursuant to still further embodiments of the present invention, the pH- and temperature-sensitive block copolymer, which is represented by the following formula:

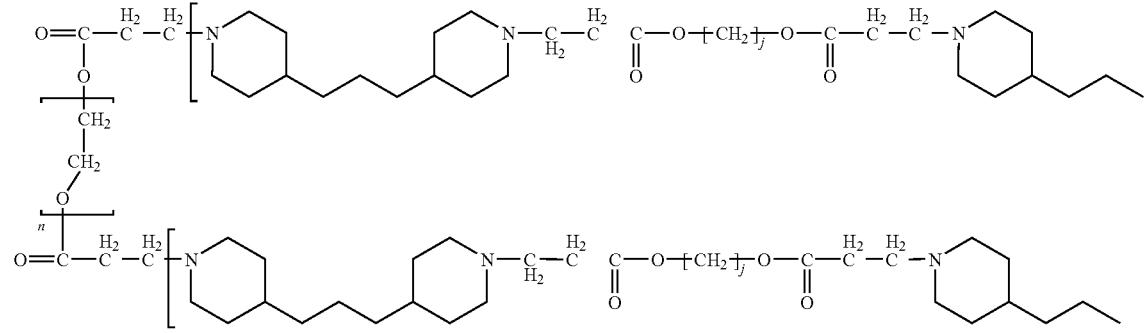

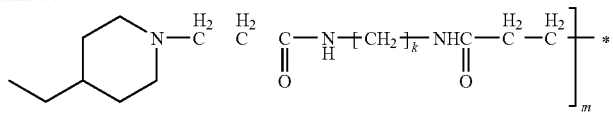

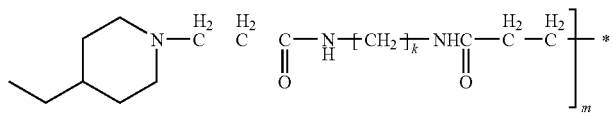

wherein j and k is a natural number ranging from 4 to 10, n is a natural number ranging from 11 to 45, and m is a natural number ranging from 10 to 100.

Pursuant to still further embodiments of the present invention, the mixture ratio of the poly (β-amino ester)-based oligomer and the poly (amido amine)-based oligomer is 1:0.05-0.50.

Pursuant to embodiments of the present invention, a method for preparing a pH- and temperature-sensitive block copolymer excellent safety comprising:
  a) forming a polyethylene glycol-based block precursor; and b) coupling the polyethylene glycol-based block precursor and poly (β-amino ester)-based oligomer, or poly (amido amine)-based oligomer, or partial mixture thereof.

Pursuant to some embodiments of the present invention, both terminal groups of polyethylene in the polyethylene glycol-based block copolymer is acrylated to be reacted with poly (β-amino ester)-based block precursor.

Pursuant to another embodiment of the present invention, the polyethylene glycol-based compound is represented by the following formula 1:

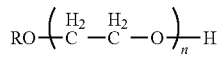

[Formula 1]

wherein R represents hydrogen or alkyl group containing 1 to 5 carbon atoms, and n is a natural number ranging from 11 to 45.

Pursuant to yet another embodiment of the present invention, the molecular weight of the polyethylene glycol-based compound is 500 to 8,000.

Pursuant to further embodiments of the present invention, the molecular weight of the polyethylene glycol (PEG) where R in the formula 1 represents hydrogen is 1,000 to 6,000.

Pursuant to still further embodiments of the present invention, the molecular weight of the methoxy polyethylene glycol (MPEG) where R in the formula 1 represents methyl group is 1,000 to 7,000.

Pursuant to still further embodiments of the present invention, forming a polyethylene glycol-based block precursor is represented by the following formula:

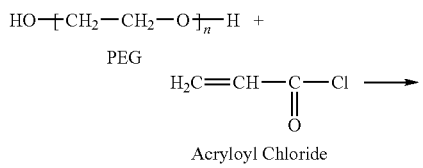

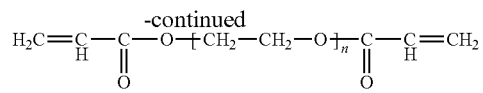

A wherein n is a natural number ranging from 11 to 45.

Pursuant to still further embodiments of the present invention, the poly (β-amino ester)-based precursor further includes at least one substituent selected from the group consisting of primary amine group, secondary amine group, and bisacrylate reacted with polyethylene glycol-based compound.

Pursuant to still further embodiments of the present invention, the poly (β-amino ester)-based oligomer is formed by polymerization of bisacrylate compound and amine compound.

Pursuant to still further embodiments of the present invention, the bisacrylate compound is represented by the following formula:

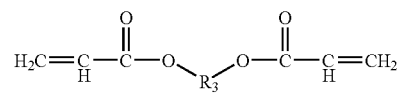

wherein $R_3$ represents alkyl group containing 1 to 30 carbon atoms.

Pursuant to still further embodiments of the present invention, the bisacrylate compound is at least one selected from the group consisting of ethylene glycol diacrylate, 1,4-butanediol diacrylate, 1,3-butanediol diacrylate, 1,6-hexane dioldiacrylate, 1,6-hexanediol ethoylate diacrylate, 1,6-hexanediol propoxylate diacrylate, trimethylol-propane triacrylate, 3-hydroxy-2,2-dimethylpropyl-hydroxy-2,2-dimethylpropyonate diacrylate, 1,7-heptanediol diacrylate, 1,8-octanediol diacrylate, 1,9-nonanediol diacrylate, 1,10-decanediol diacrylate, or mixture thereof.

Pursuant to still further embodiments of the present invention, the amine compound is the primary amine compound, di-amine compound containing the secondary amine group or the mixture thereof.

Pursuant to still further embodiments of the present invention, the primary amine compound is at least one selected from the group consisting of 4,4'-trimethyldipiperidine, 3-methyl-4-(3-methylphenyl)piperazine, 3-methylpiperazine, 4-(bis (fluorophenyl)methyl)piperazine, 4-(ethoxycarbonylmethyl)piperazine, 4-(phenylmethyl)piperazine, 4-(1,1'-dimethoxycarbonyl)piperazine, 4-{2-[bis-(2-prophenyl)amino]ethyl}piperazine, methylamine, ethylamine, butylamine, hexylamine, 2-ethylhexylamine, 2-piperidine-1-yl-ethylamine, and C-arirdine-1-yl-methylamine.

Pursuant to still further embodiments of the present invention, the di-amine compound containing the secondary amine is at least one selected from the group consisting of piperazine, 4,4'-trimethylene dipiperidine, N,N'-dimethyl ethylene diamine, N,N'-diethylene diamine, imidazolidine, and diazepine.

Pursuant to still further embodiments of the present invention, the molecular weight ratio of the bisacrylate compound and the amine compound is 1:0.5-4.0.

Pursuant to still further embodiments of the present invention, the molecular weight of poly (β-amino ester)-based oligomer or poly (amido amine)-based oligomer is 1,000 to 5,000.

Pursuant to still further embodiments of the present invention, the poly (β-amino ester)-based precursor further includes at least one substituent selected from the group consisting of primary amine group, secondary amine group, and bisacrylate reacted with polyethylene glycol-based compound.

Pursuant to still further embodiments of the present invention, the poly (β-amino ester)-based oligomer further includes functional group of hydroxyl groups (—OH), carboxyl groups (—COOH), or amine groups (—NH$_2$).

*69Pursuant to still further embodiments of the present invention, the poly (β-amino ester)-based oligomer, the poly (amido amine)-based oligomer, or partial mixture thereof includes tertiary amine group ionized under pH 7.0.

Pursuant to still further embodiments of the present invention, the block copolymer is represented by the following formula:

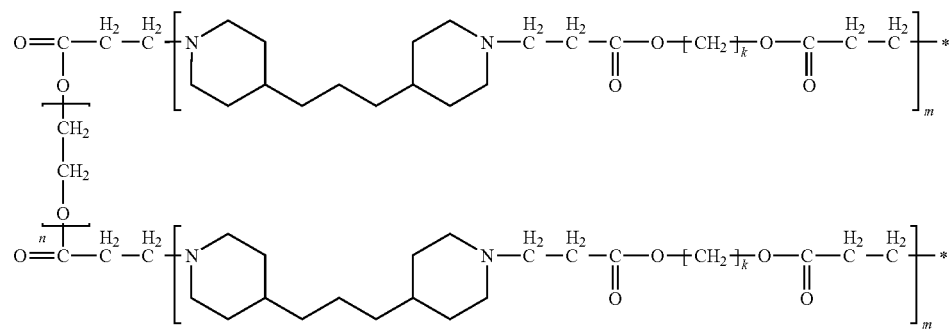

wherein k is a natural number ranging from 4 to 10, n is a natural number ranging from 11 to 45, and m is a natural number ranging from 10 to 100.

Pursuant to still further embodiments of the present invention, the molecular weight of the block copolymer is 3,000 to 32,000.

Pursuant to still further embodiments of the present invention, the molecular weight ratio of the polyethylene glycol-based compound and the poly (β-amino ester)-based oligomer is 1:1-4.

Pursuant to still further embodiments of the present invention, the block copolymer forms hydrogel at pH 7.0 to 7.4 and sol-sate pH 3.0 to under 7.0

Pursuant to still further embodiments of the present invention, the method which is prepared by mixing the acrylate polyethylene glycol with the amine compound equivalent to the precursor of the poly (β-amino ester)-based oligomer being pH-sensitive compound and bisacrylate compound and then via coupling with amine groups (—NH) and acrylate groups (—CH=CH$_2$).

Pursuant to still further embodiments of the present invention, the method which is represented by the following formula:

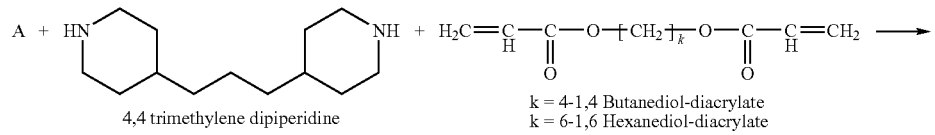

4,4 trimethylene dipiperidine k = 4-1,4 Butanediol-diacrylate
k = 6-1,6 Hexanediol-diacrylate

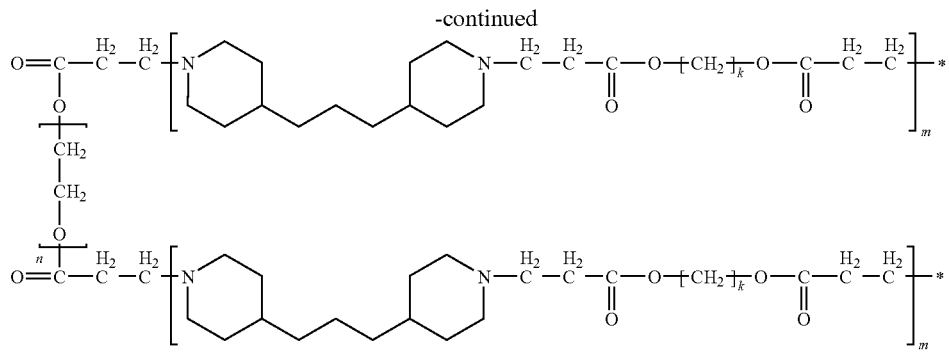

wherein k is a natural number ranging from 4 to 10, n is a natural number ranging from 11 to 45, and m is a natural number ranging from 10 to 100.

Pursuant to embodiments of the present invention, a method for preparing a pH- and temperature-sensitive block copolymer excellent safety comprising: adding a polyethylene glycol of molecular weight ranging from 1,000 to 6,000 with a acryloyilchloride to form a block copolymer having double bond; and forming a triple (PAG-PEG-PAE) copolymer by adding trimethylene dipiperidine and 1,6-hexanediol diacrylate at room temperature so as to form a (β-amino ester) block after dissolving the polyethylene glycol with double bond by adding chloroform at room temperature in a chemical reactor, wherein the molecular weight ratio of the polyethylene glycol block and the poly (?amino ester) block is 1:1-4 and total molecular weight thereof is 3,000 to 32,000.

Pursuant to some embodiments of the present invention, the poly (amido amine)-based oligomer is obtained by polymerization of bis-acrylamide compound and amine compound.

Pursuant to another embodiment of the present invention, the bis-acrylamide compound is represented by the following formula:

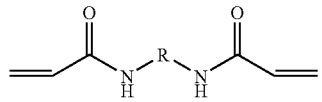

wherein R represents hydrogen or alkyl group containing 1 to 20 carbon atoms.

Pursuant to yet another embodiment of the present invention, the bis-acrylamide compound is at least one selected from the group consisting of N,N'-methylene bis-acrylamide (MDA), N,N'-ethylene bis-acrylamide, N-isopropylacrylamide, 1,4,-butylene diacrylamide, 1,6-hexylenediacrylamide, 1,8-octylene diacrylamide, 1,10-decanediacrylamide, or the mixture thereof, and wherein the diacrylamide compound and amine compound is at least one selected from the group consisting of 4-aminomethylpiperidine (AMPD), N-methylenediamine (MEDA), N-ethylenediamine (EEDA), N-hexylethylenediamine (HEDA), 1-(2-aminoethyl)piperazine (AEPZ), or the mixture thereof.

Pursuant to further embodiments of the present invention, the amine compound is the primary amine compound, di-amine compound containing the secondary amine group or the mixture thereof.

Pursuant to still further embodiments of the present invention, wherein the primary amine compound is at least one selected from the group consisting of 4,4'-trimethyldipiperidine, 3-methyl-4-(3-methylphenyl)piperazine, 3-methylpiperazine, 4-(bis (fluorophenyl)methyl)piperazine, 4-(ethoxycarbonylmethyl)piperazine, 4-(phenylmethyl)piperazine, 4-(1,1?dimethoxycarbonyl)piperazine, 4-{2-[bis-(2-prophenyl)amino]ethyl}piperazine, methylamine, ethylamine, butylamine, hexylamine, 2-ethylhexylamine, 2-piperidine-1-yl-ethylamine, and C-arirdine-1-yl-methylamine.

Pursuant to still further embodiments of the present invention, the di-amine compound containing the secondary amine is at least one selected from the group consisting of piperazine, 4,4'-trimethylene dipiperidine, N,N'-dimethyl ethylene diamine, N,N'-diethylene diamine, imidazoridine, and diazepane.

Pursuant to still further embodiments of the present invention, the acrylate polyethyleneglycol-based compound is reacted with bisacrylate compound and bis-acrylamide compound, and the molecular weight ratio thereof is 1:0.05:2 to 1:0.2:2.

Pursuant to still further embodiments of the present invention, the molecular weight of poly (β-amino ester)-based oligomer or poly (amido amine)-based oligomer is 1,000 to 5,000.

Pursuant to still further embodiments of the present invention, the method, which is represented by the following formula:

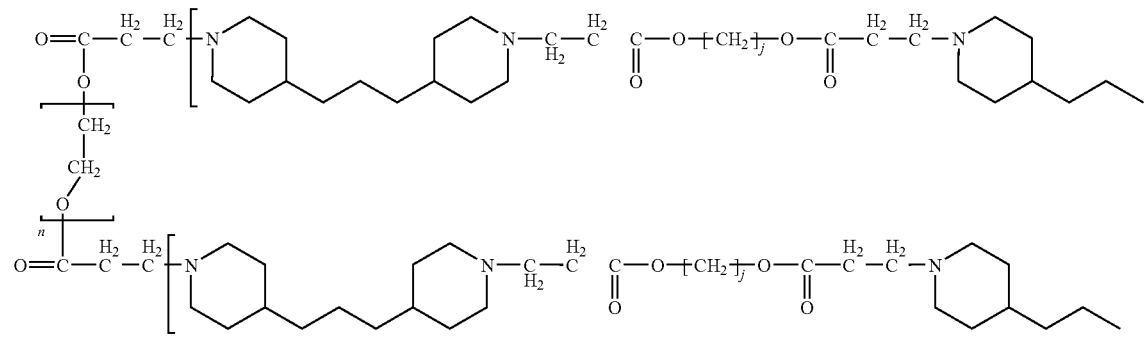

-continued

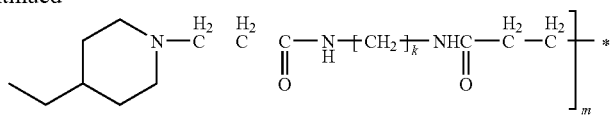

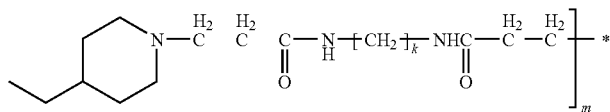

wherein k is a natural number ranging from 4 to 10, n is a natural number ranging from 11 to 45, and m is a natural number ranging from 10 to 100.

Pursuant to still further embodiments of the present invention, the molecular weight ratio of the polyethylene glycol-based compound, and the poly (β-amino ester)-based oligomer or the poly (amido amine) mixture thereof is 1:1-4.

Pursuant to still further embodiments of the present invention, the method, which is prepared by mixing the acrylate polyethylene glycol with the amine compound equivalent to the precursor of the poly (β-amino ester)-based oligomer being pH-sensitive compound, the amine compound equivalent to the precursor of the bisacrylate compound and the poly (amido amine) oligomer, and bisacrylate compound and then via coupling with amine groups (—NH) and acrylated groups (—CH=CH$_2$).

Pursuant to still further embodiments of the present invention, the method which is represented by the following formula:

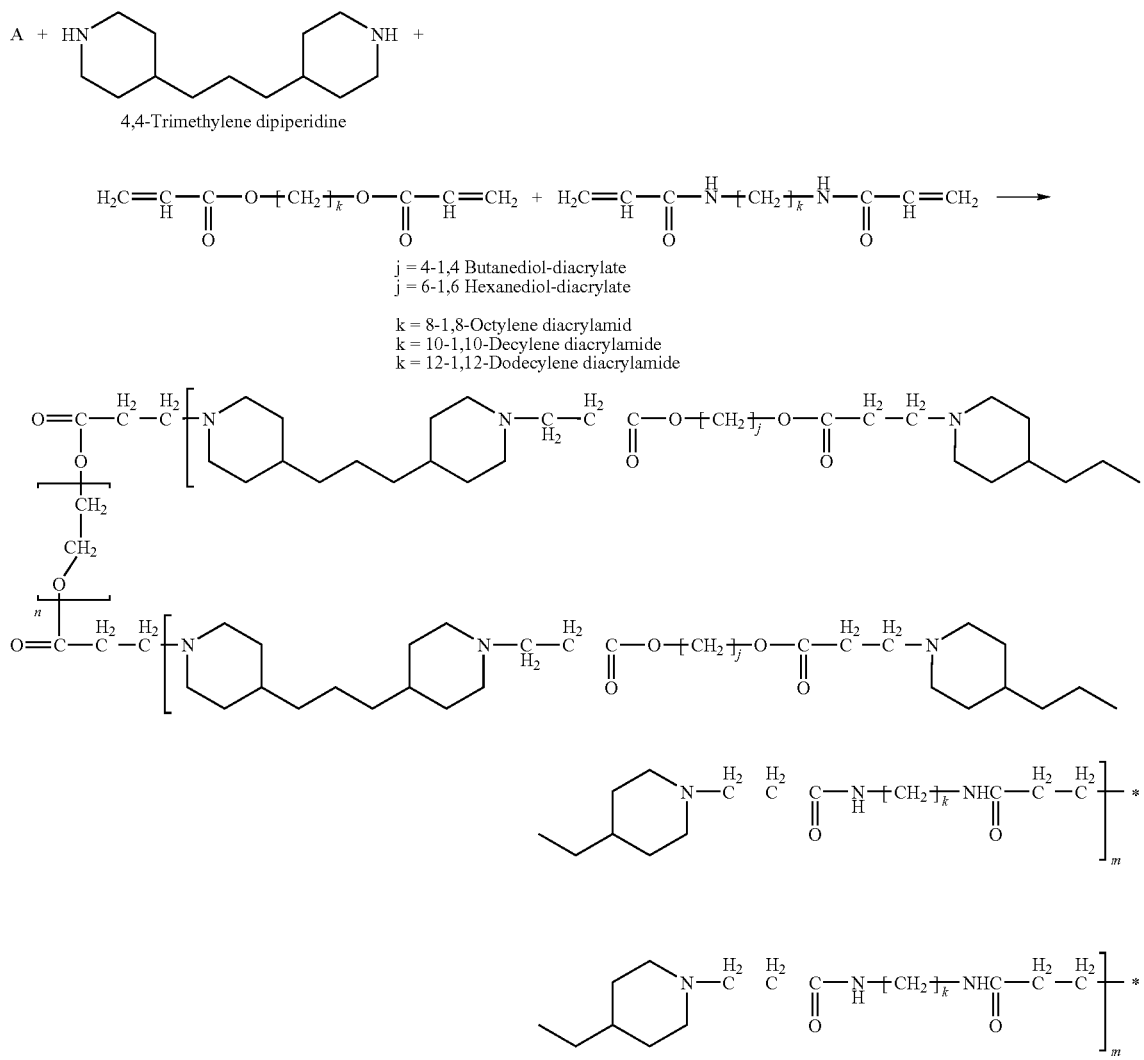

wherein k is a natural number ranging from 4 to 10, n is a natural number ranging from 11 to 45, and m is a natural number ranging from 10 to 100.

Pursuant to embodiments of the present invention, a method for preparing a pH- and temperature-sensitive block copolymer excellent safety comprising: adding a polyethylene glycol of molecular weight ranging from 1,000 to 6,000 with a acrylol chloride to form a block copolymer having double bond; and forming a triple P(AE-AA)-PEG-P(AE-AA) copolymer by adding trimethylenedipiperidine, 1,6-hexanediol diacrylate, and methyelen bis-acrylamide at room temperature so as to form a (β-amino ester) block after dissolving the polyethylene glycol with double bond by adding chloroform at room temperature in a chemical reactor, wherein the molecular weight ratio of the PEG block and the P(AE-AA) block is 1:1-4 and total molecular weight thereof is 3,000 to 32,000.

Pursuant to embodiments of the present invention, a hydrogel composition comprising a block copolymer is provided according to the block copolymer or the method for preparing a pH- and temperature-sensitive block copolymer excellent safety in vivo.

Pursuant to embodiments of the present invention, a drug carrier comprising a block copolymer is provided according to the block copolymer or the method for preparing a pH- and temperature-sensitive block copolymer excellent safety in vivo.

Pursuant to embodiments of the present invention, a drug carrier prepared according to the block copolymer or the method for preparing a pH- and temperature-sensitive block copolymer excellent safety is provided. The drug carrier comprises: a block copolymer according to any one of the claims; and bioactive materials included in the block copolymer.

Pursuant to still further embodiments of the present invention, the bioactive materials is protein such as insulin, symlin, exendin, somatokine, hGH, G-CSF, EPO, anti-cancer drug such as paclitaxal, chlorambucil, interferon, single chain Fv antibodies, monoclonal antibodies, vaccine, antimicrobial drug, steroid, anti-inflammatory drugs, sex hormone, immune retarder, antiviral drug, anesthetic, anti-emetics, or antihistamine and further includes excipient, stabilization drug, conditioner, binder, or disintergrant, wherein the compound further includes additive or solvent.

Pursuant to still further embodiments of the present invention, the drug carrier is an oral medication or non-oral medication and preferably vein, muscle, or hypodermic injection material.

Advantageous Effects

According to the scanning pH-sensitive block copolymer hydrogel with excellent safety and a drug carrier using the same, in order to dramatically improve toxicity of byproduct degraded when injected in vivo, hydrogels are obtained by coupling hydrophilic polymers with a compound comprising poly (β-amino ester) (PAE) having hydrophobicity and hyrophilicity due to degree of ionization depending on pH variations without polyester-based hydrophobic polymers, which has biodegradation but are accumulated in vivo to produce various side effects. As a result, the hydrogels have temperature sensitivity as well as pH sensitivity and can be obtained in stable.

Further, the hydrogel and the method for preparing the same according to the present invention, stable hydrogels are obtained at a specific pH range, for example, pH 7.0 to 7.4 (i.e., pH range of normal cells in the body). pH ranging 3.0 to under 7.0 (i.e., pH range of abnormal cells such as cancer cells), the hydrogels are maintained in a sol-state. Accordingly, the hydrogels are used as carriers for targeted drug delivery to cancer cells. In other words, poly (β-amino ester) (PAE) shows an increased degree of ionization, at a low pH (under pH 7.0), poly (β-amino ester) (PAE) becomes totally water-soluble because tertiary amine groups present in poly (βamino ester) (PAE) or poly (amido amine). Poly (β-amino ester) (PAE) shows an decreased degree of ionization, when pH is over 7.0, to show hydrophobicity to be maintained in a gel state. For these characteristics, multi-block copolymer can show sol-gel transition behavior sensitive to temperature as well as pH.

Further, according to the block copolymer and method for preparing the same, triblock copolymer [poly (β-amino ester-co-amido amine)-polyethylene glycol-poly (β-amino ester-co-amido amine)] is formed. Thus, there are many advantages such as controlling biodegradation rate by controlling molecular weight of each of compounds and sustained-release of drug carriers.

Further, according to the block copolymer and method for preparing the same, the pH- and temperature-sensitive block copolymer is safe in the body to be applied in the field of medical treatment, gene delivery, drug delivery, in particular, sustained drug delivery system which carries and release drugs in vivo. In addition, the pH- and temperature-sensitive block copolymer can deliver a diagnosis including abnormal cells, and thus can also be applied to the field of diagnostic imaging Further, according to the block copolymer and method for preparing the same, hydrogels are obtained at a pH range of 7.0 to 7.4, which is the same pH under the normal body conditions and the block copolymer is maintained in a sol-state under pH 7.0 and abnormal conditions such as cancer cell condition. However, in addition to the cancer cell targeted micelles, it is possible to design targeted micelles for use in the field of genetic variations, etc., by modifying the constitutional elements of the block copolymer, molar ratio and molecular weight of each constitutional element and/or functional groups in the blocks.

DESCRIPTION OF DRAWINGS

The foregoing and other objects, features and advantages of the present invention will become more apparent from the following detailed description when take in conjunction with the accompanying drawings in which.

BEST MODE

Figure 1:
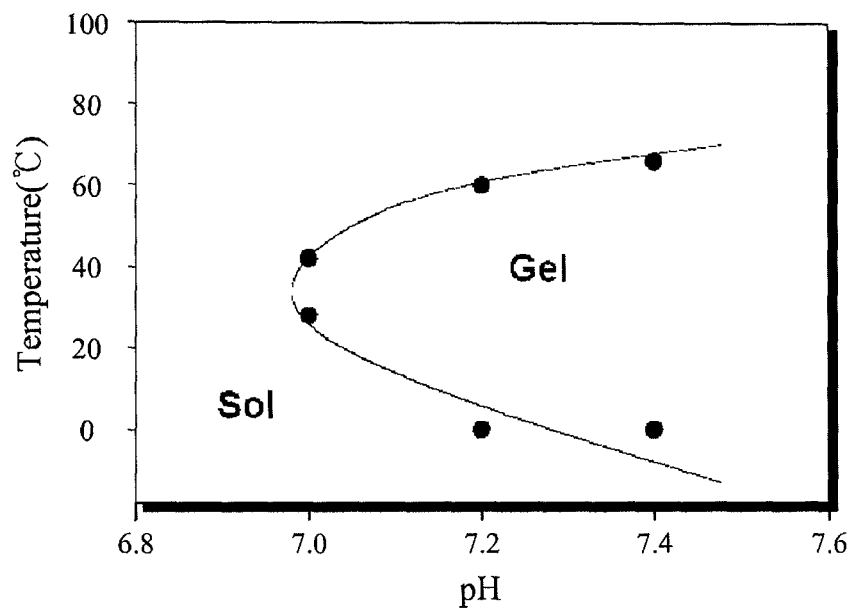
FIG. 1 is a graph showing sol-gel transition behavior of triblock copolymer comprising polyethylene glycol-based compound having temperature sensitivity and biodegradable poly (β-amino ester) compound, depending on temperature and pH variations according to a preferable embodiment of the present invention.

Embodiments of the present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

As used herein, the terms "about", "substantially" etc. are intended to allow some leeway in mathematical exactness to account for tolerances that are acceptable in the trade and to prevent any unconscientious violator from unduly taking advantage of the disclosure in which exact or absolute numerical values are given so as to help understand the invention.

The present inventors believe that in the event that only polyethylene glycol-based compound as hydrophilic block, only polylactide, polyglycolide, and polycaprolactone as hydrophobic, and temperature-sensitive block copolymer hygrogels comprising copolymer thereof are adopted, there is a high possibility that various side effects occur in a process that biodegraded byproducts when injected in vivo. To overcome these problems, a pH- and temperature-sensitive block copolymer comprising polyethylene glycol-based compound having hydrophobicity and sensitive to temperature and poly (β-amino ester) having hydrophobicity and hydrophilicity due to degree of ionization depending on pH variations is prepared. According to this block copolymer, it is completely released outside body through biodegradation when injected in vivo. In addition, many problems of temperature-sensitive hydrogels are solved by compounding the above-mentioned copolymer. Actually, it could be found that the block copolymer hydrogel shows sol-gel transition characteristic at a specific pH. The block copolymer hydrogel is gelled at pH range of 7.0 to 7.4 similar to pH range in the body, whereas it becomes in a sol-state at pH range of 7.0 to 7.4 or less. As a result, they are recognized that gel is stably formed in the body without a conventional problem in temperature-sensitive hydrogels such as the clogging phenomenon of injection needles occurring during injection. Thus, the block copolymer can be used as drug carriers for target delivery system at a specific temperature and pH. In the meanwhile, hydrogels biodegraded to be released outside body can be formed by coupling poly (β-amino ester) whose main ring is ester bond and having pH sensitivity without employing hydrophilic polymer in order to completely release pH-sensitive polymers outside body through biodegradation.

The pH- and temperature-sensitive block copolymer according to the present invention may be triblock (PAE-PEG-PAE).

One constitutional element forming the pH- and temperature-sensitive block copolymer according to the present invention is polyethylene glycol-based compound (PEG). There is no particular limitation in selection of polyethylene glycol-based compound (PEG), which is known in those skilled in the art. Particularly, PEG compound represented by the following formula 1 is preferred:

[Formula 1]

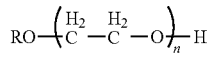

wherein R represents hydrogen or alkyl group containing 1 to 5 carbon atoms, and n is a natural number ranging from 11 to 45.

There is no particular limitation of molecular weight of PEG compound. It is preferable that the molecular weight of PEG is 500 to 8,000. Preferably, the molecular weight of the polyethylene glycol (PEG) where R in the formula 1 represents hydrogen is 1,000 to 6,000 and the molecular weight of methoxy polyethylene glycol (MPEG) where R in the formula 1 represents methyl group is 1,000 to 7,000. In case that the molecular weight of methoxy polyethylene glycol (MPEG) is not in the range of 1,000 to 7,000, that is, the molecular weight thereof is under 500 or over 8,000, it is difficult to form gel. Even if gel is formed, it does not may used as a carrier for actual drug delivery system due to weakness of gel intensity.

There is no particular limitation in selection of polyethylene glycol compound as long as it contains the above compounds, but it is preferable that both ends thereof is acrylate combination so as to react with primary amine group and secondary amine group of poly (β-amino ester)-based block. There is no particular limitation in selection of another constitutional element of forming the pH- and temperature-sensitive block copolymer according to the present invention if the element is compound exhibiting various degree of ionization depending on pH variations. Preferably, the element is oligomer having hydrophobicity as well as pH sensitivity.

The poly (β-amino ester)-based oligomer is reacted with polyethylene glycol compound as a precursor, which further includes at least one substituent selected from the group consisting of primary amine group, secondary amine group, and bisacrylate reacted with polyethylene glycol-based compound.

The above poly (β-amino ester)-based compound includes tertiary amines group ionized under pH 7.0 to exhibit pH sensitivity in the body. The poly (β-amino ester)-based oligomer preferably includes functional group of hydroxyl groups (—OH), carboxyl groups (—COOH), or amine groups (—NH$_2$). The reason for this is to easily make the block copolymer according to the present invention by copolymerization reaction.

Since the poly (β-amino ester)-based (PAE) oligomer has ionization characteristic in which solubility changed with respect to water depending on pH variation due to the presence of tertiary amine group in itself, as above mentioned, it may form hydrogels depending on pH variation or is maintained in a sol-state. The above compounds may be prepared by a process known to one skilled in the art. In one embodiment of such processes, bisacrylate compound having a double bond is polymerized with an amine compound via Michael reaction mechanism to produce a poly (β-amino ester)-based oligomer.

The bisacrylate compound used in the above process may be represented by the following formula 2, and non-limiting examples of such bisacrylate compounds include at least one selected from the group consisting of ethylene glycol diacrylate, 1,4-butanediol diacrylate, 1,3-butanediol diacrylate, 1,6-hexanediol diacrylate, 1,6-hexanediol ethoylate diacrylate, 1,6-hexanediol propoxylate diacrylate, trimethylol-propane triacrylate, 3-hydroxy-2,2-dimethylpropyl-hydroxy-2, 2-dimethylpropyonate diacrylate, 1,7-heptanediol diacrylate, 1,8-octanediol diacrylate, 1,9-nonanediol diacrylate, 1,10-decanediol diacrylate, or mixture thereof.

[Formula 2]

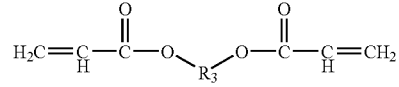

wherein R₃ represents alkyl group containing 1 to 30 carbon atoms

Additionally, there is no particular limitation in selection of the amine compound as long as it contains an amine group. Preferably, a primary amine represented by the following formula 3, a secondary amine-containing diamine compound the mixture thereof represented by the following formula 4, etc., are used.

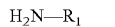  [Formula 3]

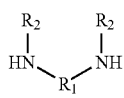  [Formula 4]

wherein $R_1$ and $R_2$ represent alkyl group containing 1 to 20 carbon atoms

*143Non-limiting examples of such primary amine compounds include at least one selected from the group consisting of 4,4'-trimethyldipiperidine, 3-methyl-4-(3-methylphenyl)piperazine, 3-methylpiperazine, 4-[bis(fluorophenyl)methyl]piperazine, 4-(ethoxycarbonylmethyl)piperazine, 4-(phenylmethyl)piperazine, 4-(1,1'-dimethoxycarbonyl)piperazine, 4-{2-[bis-(2-prophenyl)amino]ethyl}piperazine, methylamine, ethylamine, butylamine, hexylamine, 2-ethylhexylamine, 2-piperidine-1-yl-ethylamine, and C-arirdine-1-yl-methylamine.

When preparing a pH-sensitive poly (β-amino ester)-based oligomer, the bisacrylate compound is reacted with the amine compound preferably in a molar ratio of 1:0.5 to 4.0. When the molar ratio of the amine compound is under 0.5 or over 4.0, it is difficult to control block length of the block copolymer as well as to drop pH sensitivity due to broad molecular weight distribution.

The molecular weight of the poly (β-amino ester)-based oligomer is not limited at a special range, but preferably 1,000 to 5,000. When the molecular weight thereof is under 1,000, the block copolymer will not show a sol-gel transition behavior caused by a change in pH. When it is over 5,000, the block copolymer will be difficult to exhibit pH sensitivity as well.

The inventive copolymer formed by coupling the above-described components (i.e., the copolymer of the PEG-based compound (A) with the poly (β-amino ester)-based oligomer (B)) to each other is preferably in the form of a triblock copolymer. Specific example of the triblock copolymer is represented by the following formula 5 wherein k is a natural number ranging from 4 to 10, n is a natural number ranging from 11 to 45, and m is a natural number ranging from 10 to 100.

The block copolymer represented by the above formula 5 forms hydrogels or maintains a sol state depending on pH variations due to amphiphilicity and pH sensitivity. Particularly, the block copolymer according to the present invention can be used satisfactorily in various applications requiring sensitivity depending on pH variations in the body (for example, carriers for drug delivery).

Although there is no particular limitation in molecular weight of the block copolymer, it is preferable that the block copolymer has a molecular weight of 3,000 to 32,000. In order to make a block copolymer sensitive to temperature, polyethylene glycol having a molecular weight of 500 to 8,000 is adopted. At this time, it is preferable that the molecular weight ratio of hydrophilic block and hydrophobic block is 1:1 to 4. When the molecular weight ratio of them is less than 1:1, it is difficult to form gel. To the contrary, when the molecular weight ratio of them is over 1:4, there is a problem that the magnitude of hydrophobicity of the block copolymer will be increased such that the block copolymer can not dissolved in water.

The pH- and temperature-sensitive block copolymer according to the present invention may further comprise other units or additives generally known to one skilled in the art, in the scope of the present invention.

To obtain the pH- and temperature-sensitive block copolymer according to the present invention by employing the PEG-based compound and the poly (β-amino ester)-based oligomer, one or combination method of a conventional method such as Michael reaction mechanism, cationic copolymerization, anion copolymerization, and condensation polymerization, which are known in one skilled in the art, may be used.

For instance, a method for preparing a pH- and temperature-sensitive block copolymer comprises the steps of: a) reacting a PEG-based compound with a acryloyl chloride; and b) coupling the acrylated PEG with a poly (β-amino ester)-based oligomer.

First, a PEG precursor introducing acrylate group is formed so as to coupling the PEG-based compound with the poly (β-amino ester)-based oligomer. This polymerization reaction can be illustrated the following reaction scheme 1:

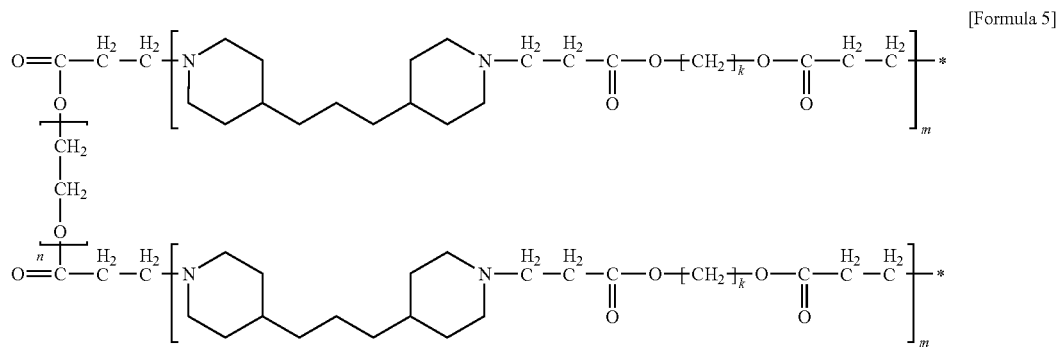

[Formula 5]

[Reaction Scheme 1]

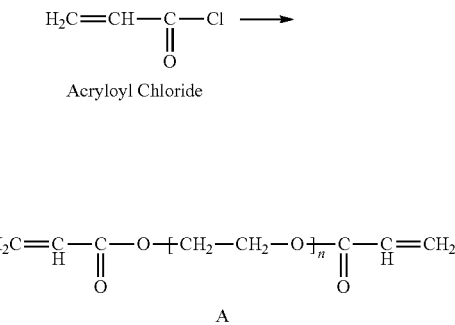

wherein n is natural number ranging from 11 to 45.

In one embodiment of the method according to the above reaction scheme 1, the resultant acrylated PEG compound is mixed with amine compound being the precursor of the poly (β-amino ester)-based oligomer (i.e., dipiperadine) and bisacrylate, which are equivalent to pH-sensitive compound. Then, by coupling amine group (—NH) and acrylate group (—CH=CH$_2$), a pH- and temperature-sensitive triblock copolymer may be prepared, and this reaction scheme is represented by the following reaction scheme 2:

wherein k is a natural number ranging from 4 to 10, n is a natural number ranging from 11 to 45, and m is a natural number ranging from 10 to 100.

The reaction temperature and time in the above reaction scheme 2 are not specifically limited. Primary amine compound and secondary amine compound used to prepare the poly (β-amino ester)-based oligomer is the same as aforementioned. In addition, it is preferable that bisacrylate compound reacted with the above compound to form a poly (β-amino ester) block is ethylene glycol diacrylate, 1,4-butanediol diacrylate, 1,3-butanediol diacrylate, 1,6-hexanediol diacrylate, 1,6-hexanediol ethoylate diacrylate, 1,6-hexanediol propoxylate diacrylate, trimethylol-propane triacrylate, 3-hydroxy-2,2-dimethylpropyl-hydroxy-2,2-dimethylpropyonate diacrylate, 1,7-heptanediol diacrylate, 1,8-octanediol diacrylate, 1,9-nonanediol diacrylate, 1,10-decanediol diacrylate, or its derivatives such as diol diacrylate-based compound (CH$_2$=CH—CO—R—CO—CH=CH$_2$).

Meanwhile, the block copolymer according to the present invention can be obtained by only the poly (amido amine)-based compound having an amide bond instead of an ester bond of the poly (β-amino ester)-based compound or coupling the poly (β-amino ester)-based compound with the poly (amido amine)-based oligomer in order to controlling biodegradation rate.

Concretely, the pH- and temperature-sensitive block copolymer according to the present invention can be prepared by mixing the acrylated polyethylene glycol with the amine compound equivalent to the precursor of the poly (β-amino ester)-based oligomer being pH-sensitive compound and bisacrylate compound and then via coupling with amine groups (—NH) and acrylate groups (—CH=CH$_2$). This copolymer structure and reaction may be represented by the following formula 6 and reaction scheme 3, respectively.

In other words, a bisacrylate compound, a bisacrylamide compound, and an amine compound can be reacted with the acrylated polyethylene glycol compound (A).

[Reaction Scheme 2]

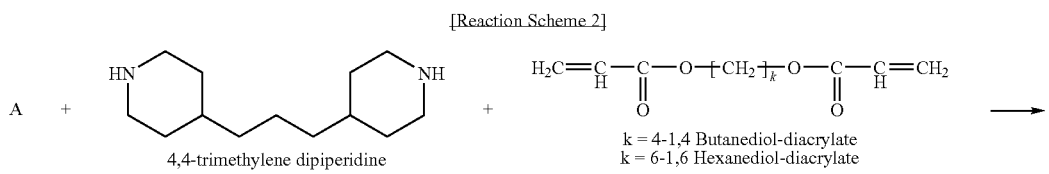

k = 4-1,4 Butanediol-diacrylate
k = 6-1,6 Hexanediol-diacrylate

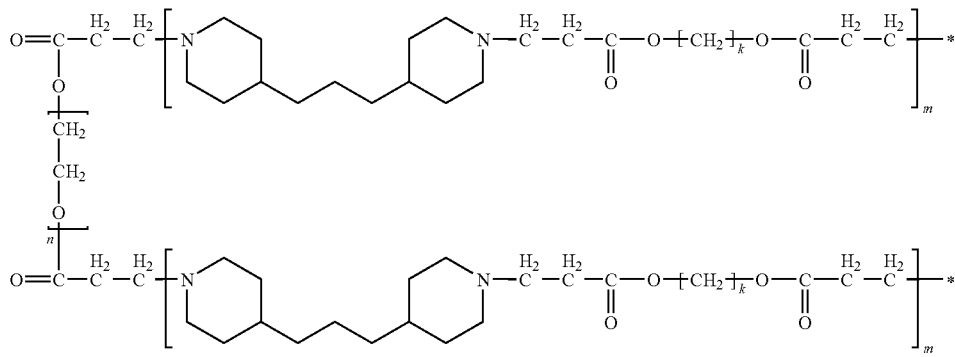

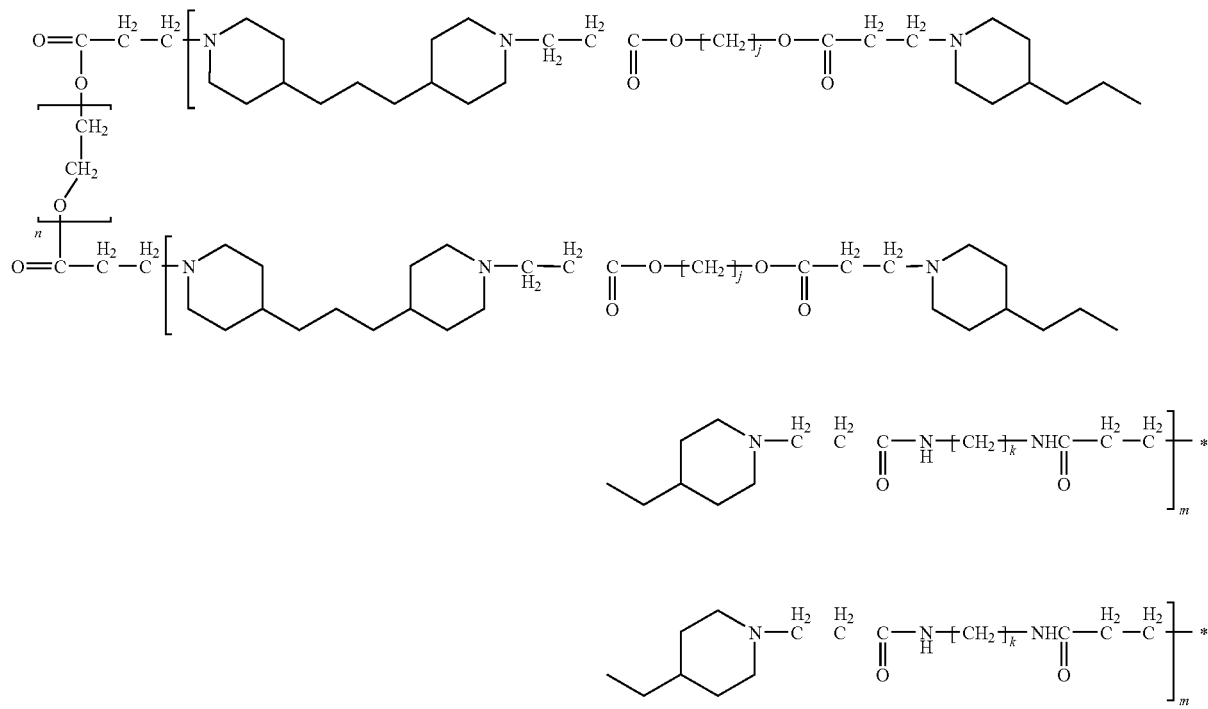
wherein k is a natural number ranging from 4 to 10, n is a natural number ranging from 11 to 45, and m is a natural number ranging from 10 to 100.
[Reaction Scheme 3]
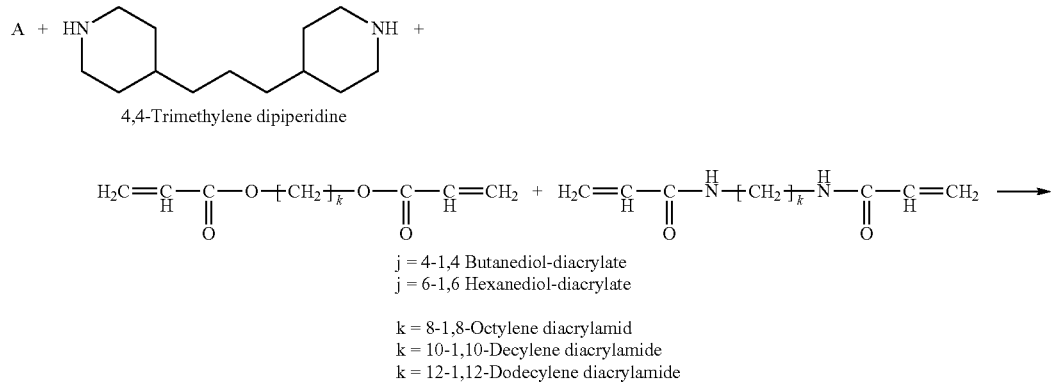
j = 4-1,4 Butanediol-diacrylate
j = 6-1,6 Hexanediol-diacrylate
k = 8-1,8-Octylene diacrylamid
k = 10-1,10-Decylene diacrylamide
k = 12-1,12-Dodecylene diacrylamide
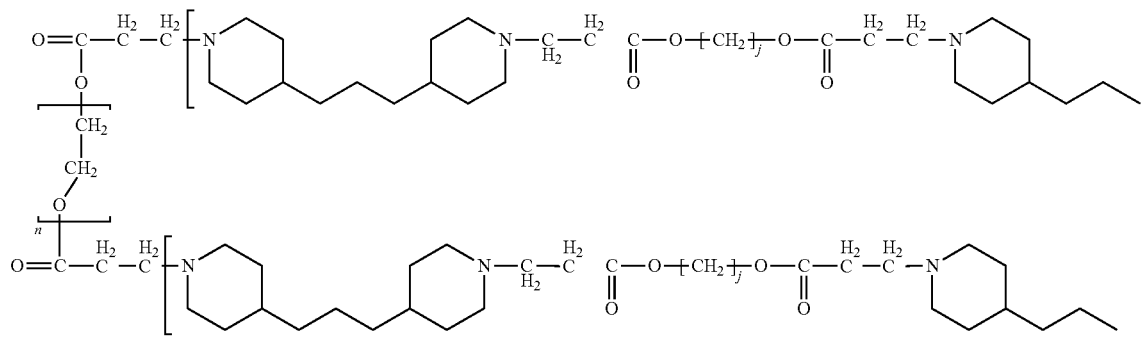

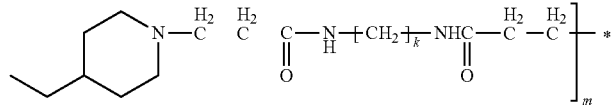

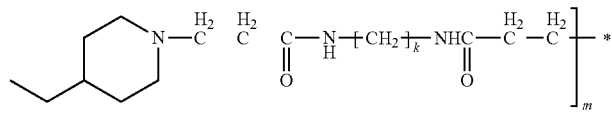

wherein k is a natural number ranging from 4 to 10, n is a natural number ranging from 11 to 45, and m is a natural number ranging from 10 to 100.

The molar ratio of the bisacrylate compound, the bisacrylamide compound, and the amine compound may be 1:0.05:0.5 to 2:0.2:2. When it is under the above ratio, controlling biodegradation rate is considered as insignificant. To the contrary, when the above ratio is greater, there are disadvantageous in that biodegradation rate is dramatically delayed, and bisacrylamide is not copolymerized with the poly (β-amino ester) block.

The poly (β-amido amine)-based oligomer may be obtained by copolymerization of the bisacrylamide compound and the amine compound. More concretely, poly (β-amido amine)-based oligomer may further include at least one substituent selected from the group consisting of primary amine group, secondary amine group, and bisacrylate reacted with polyethylene glycol-based compound via Michael reaction mechanism. Additionally, there is no particular limitation in the amine compound as long as it contains amine group. Preferably, a primary amine represented by the following formula 3, a secondary amine-containing diamine compound the mixture thereof represented by the following formula 4, etc., are used. Non-limiting examples are the same as the aforementioned.

[Formula 7]

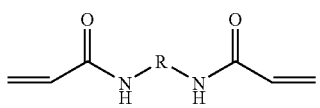

wherein R represents hydrogen or alkyl group containing 1 to 20 carbon atoms.

The reaction temperature and time in the above reaction scheme 2 are not specifically limited. Primary amine compound and secondary amine compound used to prepare the poly (β-amino ester)-based oligomer are the same as aforementioned. In addition, non-limiting examples of bisacrylate compound reacted with the above compound to form a poly (β-amino ester) block is N,N'-methylene bis-acrylamide (MDA), N,N'-ethylene bis-acrylamide, N-isopropylacrylamide, 1,4,-butylene diacrylamide, 1,6-hexylenediacrylamide, 1,8-octylene diacrylamide, 1,10-decanediacrylamide, or the mixture thereof. The diacrylamide compound and amine compound is at least one selected from the group consisting of 4-aminomethylpiperidine (AMPD), N-methylenediamine (MEDA), N-ethylenediamine (EEDA), N-hexylethylenediamine (HEDA), 1-(2-aminoethyl)piperazine (AEPZ), or the mixture thereof.

The poly (amido amine) may show pH sensitivity in the body by including tertiary amines group that is ionized under pH 7.0.

Preferably, the molecular weight of the polyethylene glycol compound and the mixture block of the poly (β-amino ester) and the poly (amido amine) is 1:1 to 4.

It is preferable that the block copolymer has a molecular weight ranging from 3,000 to 32,000. The mixture ratio of the poly (β-amino ester) and the poly (amido amine) is 1:0.05 to 0.50. When the mixture ratio is under the above ratio, controlling biodegradation rate is considered as insignificant. To the contrary, when the above mixture ratio is over the above ratio, there are disadvantageous in that biodegradation rate is dramatically delayed, and bisacrylamide is not copolymerized with the poly (β-amino ester) block.

The multi-block copolymer prepared by the above-mentioned method can show sensitivity to not only temperature but also pH, because it is in a form where the hydrophilic block, the hydrophobic block, and only the poly (β-amino ester)-based oligomer or it combination with the poly (amido amine) which shows a change in degree of ionization with a change in pH, are coupled with each other as described above.

Actually, in the poly (β-amino ester)-polyethylene glycol-the poly (β-amino ester)-triblock copolymer and the poly (β-amino ester-co-amido amine)-polyethylene glycol-the poly (β-amino ester-co-amido amine)-triblock copolymer prepared by the above-described method, the introduction of functional groups and the reaction of terminal groups could be confirmed by FT-IR and $^1$H-NMR. Also, it could be confirmed by gel permeation chromatography (GPC) that the molecular weight of the block copolymer was increased, indicating that the copolymer of the PEG-based compound with biodegradable polymer and the poly (β-amino ester)-based oligomer were coupled with each other. Also, in order to determine if the block copolymer has pH sensitivity, a change in sol-gel transition behavior was measured while changing pH with temperature, and the measurement results demonstrated that the inventive triblock copolymer has pH-sensitive characteristics (See FIGS. 1 and 2).

In another aspect, the present invention provides a hydrogel-type drug composition comprising a pH- and temperature-sensitive block copolymer and bioactive materials included in the block copolymer.

There is no particular limitation in the bioactive materials. Non-limiting examples of such bioactive materials are protein such as insulin, symlin, exendin, somatokine, hGH, G-CSF, EPO, anti-cancer drug such as paclitaxal, chlorambucil, interferon, single chain Fv antibodies, monoclonal antibodies, vaccine, antimicrobial drug, steroid, anti-inflammatory drugs, sex hormone, immune retarder, antiviral drug, anesthetic, antiemetics, or antihistamine and further includes excipient, stabilization drug, conditioner, binder, or disintergrant. In this case, the composition may further include additive or solvent that is known in one skilled in the art.

In addition, the hydrogel-type drug composition may be used an oral medication or non-oral medication or vein, muscle, or hypodermic injection material.

Furthermore, according to the present invention, there is provided used of the pH-sensitive block copolymer as carriers for drug delivery or medical diagnosis and therapy. Herein, any materials are encapsulated with the block copolymer, as long as for treatment, prevention or diagnosis of diseases.

MODE FOR INVENTION

Reference will be made in detail to the preferred embodiments of the present invention. It is to be understood that the following examples are illustrative only and the present invention is not limited thereto.

EXAMPLES

Examples 1~11

Preparation of Temperature and pH-Sensitive Triblock Copolymer

Example 1

Preparation of Poly (β-amino ester)-Polyethylene glycol-Poly (β-amino ester) Block Copolymer (PAE-PEG-PAE)

10 g of polyethylene glycol (PEG2000, Mn=2,000) and 0.2 g of catalyst stannous octoate were placed into a reactor and dried under vacuum at 110° C. for 4 hours to remove moisture. After adding 0.198 g of acryloyl chloride to the dried polyethylene glycol of 0.1 g, polyethylene glycol having a double bond of both ends thereof is obtained. The reaction mixture was performed in ice-bath under a nitrogen atmosphere, followed by the polymerization for 24 hours. After completion of the reaction, the reaction mixture was precipitated in ethyl ether to remove unreacted substance. The precipitated reaction mixture was filtered and dried under vacuum, at room temperature, thereby obtaining above polyethylene glycol. The yield of the product was more than 80%.

Meanwhile, the resultant polyethylene glycol having a double bond was dissolved by adding chloroform at room temperature into a reactor. In order to form β-amino-ester block, the resultant polyethylene glycol was dissolved by adding trimethylene dipiperadine and 1,6-hexanediol diacrylate and then reacted at 50° C. for 48 hours. After completion of the reaction, the reaction mixture was precipitated in an excess of ethyl ether to remove unreacted substance. The precipitated reaction mixture was filtered, thereby obtaining a triblock (PAE-PEG-PAE) copolymer where a poly (β-amino ester) block has a molecular weight of 4,000 and a polyethylene glycol block has a molecular weight of 2,000 and having a number-average molecular weight of 6,000. The yield of the product was more than 70%.

Example 2

Example 1 is repeated to obtain PAE-PEG-PAE block copolymer having a molecular weight of 5,000, except that PEG block has a molecular weight of 1,000. The yield of the product is more than 70%.

Example 3

Example 1 is repeated to obtain PAE-PEG-PAE block copolymer having a molecular weight of 7,000, except that PEG block has a molecular weight of 3,000. The yield of the product is more than 70%.

Example 4

Example 1 is repeated to obtain PAE-PEG-PAE block copolymer having a molecular weight of 9,000, except that PEG block has a molecular weight of 5,000. The yield of the product is more than 65%.

Example 5

Preparation of Poly (amido amine)-Polyethylene glycol-Poly (amido amine) Block Copolymer (PAA-PEG-PAA)

10 g of polyethylene glycol (PEG2000, Mn=2,000) and 0.2 g of catalyst stannous octoate were placed into a reactor and dried under vacuum at 110° C. for 4 hours to remove moisture. After adding 0.198 g of acryloyl chloride to the dried polyethylene glycol of 0.1 g, polyethylene glycol having a double bond of both ends thereof is obtained. The reaction mixture was performed in ice-bath under a nitrogen atmosphere, followed by the polymerization for 24 hours. After completion of the reaction, the reaction mixture was precipitated in ethyl ether to remove unreacted substance. The precipitated reaction mixture was filtered and dried under vacuum at room temperature, thereby obtaining the above polyethylene glycol. The yield of the product was more than 80%.

Meanwhile, the resultant polyethylene glycol having a double bond was dissolved by adding methylene chloride at room temperature into a reactor. In order to form aminoamine block, the resultant polyethylene glycol was dissolved by adding trimethylene dipiperadine and methylene bisacrylamide and then reacted at 50° C. for 48 hours. After completion of the reaction, the reaction mixture was precipitated in an excess of ethyl ether to remove unreacted substance. The precipitated reaction mixture was filtered, thereby obtaining a triblock (PAE-PEG-PAE) copolymer where a poly (amido amine) block has a molecular weight of 2,400 and a polyethylene glycol block has a molecular weight of 2,000 and having a number-average molecular weight of 4,600. The yield of the product was more than 65%.

Example 6

Example 5 is repeated to obtain PAA-PEG-PAA block copolymer having a molecular weight of 6000, except that poly (amido amine) block has a molecular weight of 4,000. The yield of the product is more than 65%.

Example 7

Example 5 is repeated to obtain PAA-PEG-PAA block copolymer having a molecular weight of 7,400, except that polyethylene glycol block has a molecular weight of 5,000. The yield of the product is more than 60%.

Example 8

Example 5 is repeated to obtain PAA-PEG-PAA block copolymer having a molecular weight of 9,000, except that polyethylene glycol block has a molecular weight of 5,000 and poly (amido amine) block has a molecular weight of 4,000. The yield of the product is more than 60%.

Example 9

Preparation of Poly (β-amino-ester-co-amido-amine)-Polyethylene glycol-Poly (β-amino-ester-co-amido-amine) Block Copolymer [(P(AE-AA)-PEG-P(AE-AA))

10 g of polyethylene glycol (PEG2000, Mn=2,000) and 0.2 g of catalyst stannous octoate were placed into a reactor and dried under vacuum at 110° C. for 4 hours to remove moisture. After adding 0.198 g of acryloyl chloride to the dried polyethylene glycol of 0.1 g, polyethylene glycol having a double bond of both ends thereof is obtained. The reaction mixture was performed in ice-bath under a nitrogen atmosphere, followed by the polymerization for 24 hours. After completion of the reaction, the reaction mixture was precipitated in ethyl ether to remove unreacted substance. The precipitated reaction mixture was filtered and dried under vacuum at room temperature, thereby obtaining the above polyethylene glycol. The yield of the product was more than 80%.

Meanwhile, the resultant polyethylene glycol having a double bond was dissolved by adding methylene chloride at room temperature into a reactor. In order to form β-amino-ester block and amido-amine block, the resultant polyethylene glycol was dissolved by adding trimethylene dipiperadine, 1,6-hexanediol diacrylate, and methylene bisacrylamide and then reacted at 50° C. for 48 hours. After completion of the reaction, the reaction mixture was precipitated in an excess of ethyl ether to remove unreacted substance. The precipitated reaction mixture was filtered, thereby obtaining P(AE-AA)-PEG-P(AE-AA) block copolymer where a poly (β-amino-ester) block has a molecular weight of 3,500, a poly (amido amine) block has a molecular weight of 500, and a polyethylene glycol block has a molecular weight of 2,000 and having a number-average molecular weight of 6,000. The yield of the product was more than 60%.

*223 Example 10

Example 9 is repeated to obtain P(AE-AA)-PEG-P(AE-AA) block copolymer having a molecular weight of 6,000, except that poly (β-amino-ester) block has a molecular weight of 3,000, and poly (amido-amine) block has a molecular weight of 1,000. The yield of the product is more than 60%.

Example 11

Example 9 is repeated to obtain P(AE-AA)-PEG-P(AE-AA) block copolymer having a molecular weight of 6,000, except that poly (β-amino-ester) block has a molecular weight of 2,000, and poly (amido-amine) block has a molecular weight of 2,000. The yield of the product is more than 60%.

Comparative Example 1

Polycaprolactone-polylatic acid having hydrophobic block is reacted with polyethylene glycol using ring-opening copolymerization, and PCLA-PEG-PCLA triblock copolymer in which both ends thereof become acrylated was prepared by adding the product with acryl chloride. The PCLA-PEG-PCLA triblock copolymer was dissolved by adding trimethylene dipiperadine and 1,6-hexanediol diacrylate that is equivalent to a precursor of amino ester at room temperature and then reacted at 50° C. for 48 hours. Example 1 is repeated to obtain PAE-PCLA-PEG-PCLA-PAE block copolymer having a molecular weight of 8,000, except that PAE-PCLA-PEG-PCLA-PAE has a molecular weight of 8,000. The yield of the product is more than 70%.

Comparative Example 2

Example 1 is repeated to obtain PAE-PEG-PAE block copolymer having a molecular weight of 4,500, except that PEG has a molecular weight of 500. The yield of the product is more than 40%.

Comparative Example 3

Example 1 is repeated to obtain PAE-PEG-PAE block copolymer having a molecular weight of 13,000, except that PEG has a molecular weight of 9,000. The yield of the product is more than 40%.

Comparative Example 4

Example 1 is repeated to obtain PAE-PEG-PAE block copolymer having a molecular weight of 3,000, except that poly (β-amino-ester) block has a molecular weight of 1,000. The yield of the product is more than 67%.

Comparative Example 5

Example 1 is repeated to obtain PAE-PEG-PAE block copolymer having a molecular weight of 7,000, except that poly (?amino-ester) block has a molecular weight of 3,000. The yield of the product is more than 50%.

Comparative Example 6

Comparative example 1 is repeated, except that polyethylene imine has a molecular weight of 2,000 so as to compare cell cytotoxicity poly (?amino-ester) having pH sensitivity.

Experimental Example 1

Evaluation of Sol-Gel Transition Behavior Depending on pH Variations

The block copolymers prepared according to the present invention was evaluated for their sol-gel transition behavior caused by a change in temperature and pH.

Each of the triblock copolymers prepared in Examples 1 to 11 was added and dissolved in a buffer solution at 10 weight % by weight and titrated with NaOH solution at 50° C. to adjust the pHs of the block copolymer solutions 5.5, 6.0, 6.5, 7.0, and 7.5. Each of the triblock copolymer solutions with the respective pHs was equilibrated at constant temperature for 10 minutes while increasing the solution temperature by 2° C. each time and then slanted to measure the sol-gel transition behavior. The sol-gel transition behaviors of the block copolymers cased by changes in temperature and pH, will be described with reference to FIG. 1.

Figure 2:
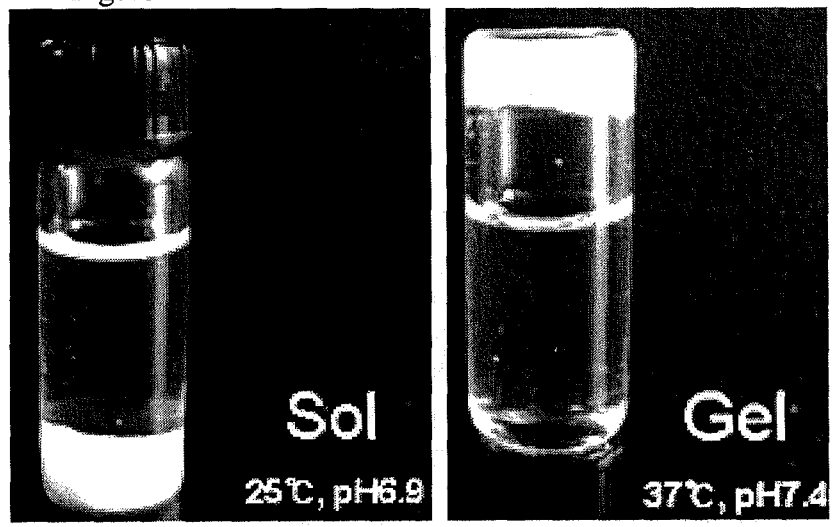
FIG. 2 depicts photographs showing sol-gel transition behavior according to Example 1, depending on temperature and pH variations.
Figure 3:
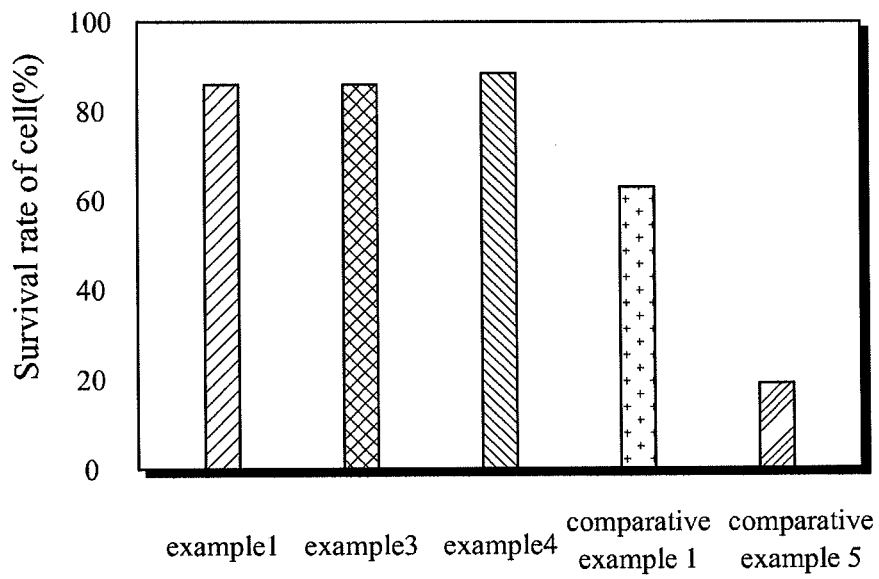
FIG. 3 is a graph showing the result of cell cytotoxicity analysis of Examples 1, 3, and 4, and Comparative Examples 1 and 5.
Figure 4:
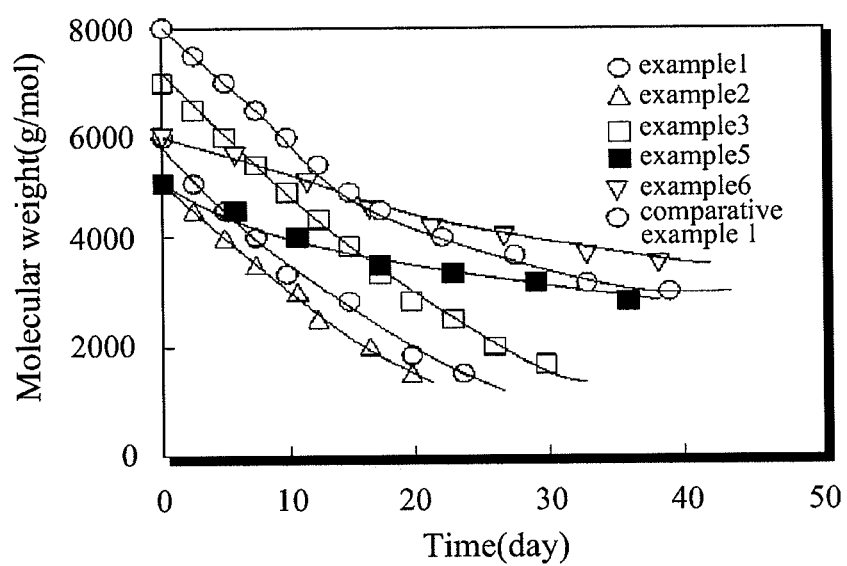
FIG. 4 is a graph showing a change of molecular weight of each of the block copolymers according to Examples 1,2,3,5, and 6, and Comparative Example 1 with the variation of time.
Figure 5:
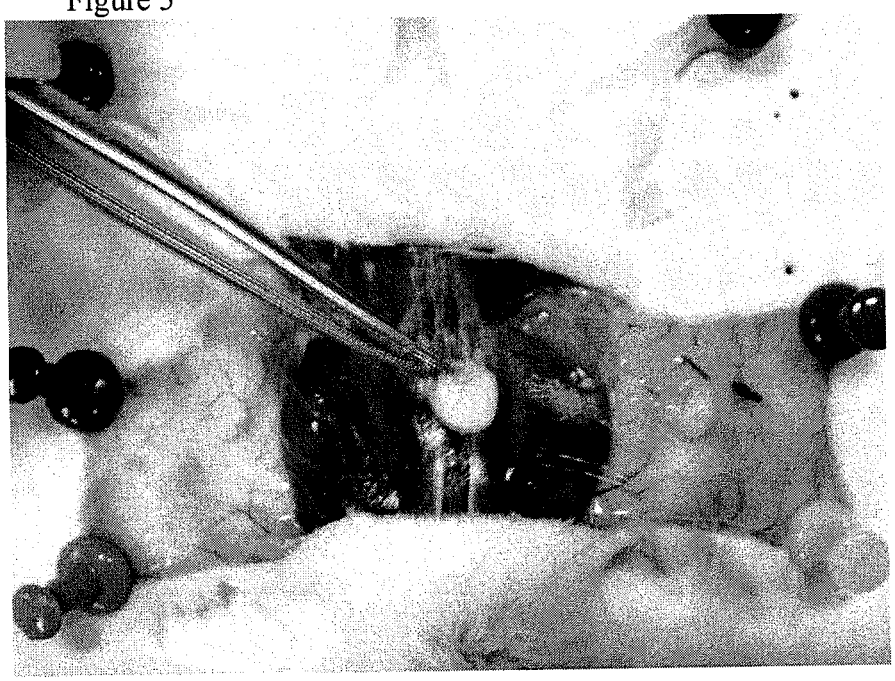
FIG. 5 is a photograph showing gel transition as 5 minutes passed after injecting triblock copolymer according to Example 1 into rat.

As shown in FIG. 1, it could be found that the inventive block copolymer showed reversible sol-gel transition behavior not only a change in the degree of ionization of poly (β-amino-ester)-based oligomer in pH but also by a change in the hydrophobicity of the biodegradable copolymer with a change in temperature. This indicated that the inventive block copolymer caused by changes in not only temperature but also pH.

Experimental Example 2

Evaluation of Cell Cytotoxicity in Example and Comparative Example

The following experiment was carried out employing shelline NIH 3T3 fibroblast method. DMEM (90% Dulbecco's modified Eagle's medium, 10% fetal calf serum, penicillin 100 units/mL, streptomycin 100 μg/mL) was used as culture medium. XTT analysis is performed employing 2,3-bis(2-methoxy-4-nitro-5-susfophenyl)-2H-tetrazolium-5-carboxanilide). 96-well plate and incubator was evaluated in Microplate reader.

After the evaluation, it could be seen that survival rate of cells becomes improved as much as 10% to 50% as compared to comparative examples.

Experimental Example 3

Evaluation of Sol-Gel Transition Behavior after Injection In Vivo

By selecting experimental rat (150 g), each of the triblock copolymers prepared in Examples 1 was added and dissolved in a buffer solution at 30% by weight and titrated with NaOH solution at 50° C. to adjust the pHs of the block copolymer solutions 6.5. Then, after injecting experimental rat, sol-gel transition behavior was observed with the lapse of time.

Although the present invention has been described herein with reference to the foregoing embodiments and the accompanying drawings, the scope of the present invention is defined by the claims that follow. Accordingly, those skilled in the art will appreciate that various substitutions, modifications and changes are possible, without departing from the spirit of the present invention as disclosed in the accompanying claims. It is to be understood that such substitutions, modifications and changes are within the scope of the present invention.

The invention claimed is:

1. A pH- and temperature-sensitive B-A-B block copolymer with excellent safety obtained by copolymerization of:
   (a) polyethylene glycol-based compound (A); and
   (b) poly (β-amino ester)-based oligomer (B),
   wherein the block copolymer is represented by the following formula:

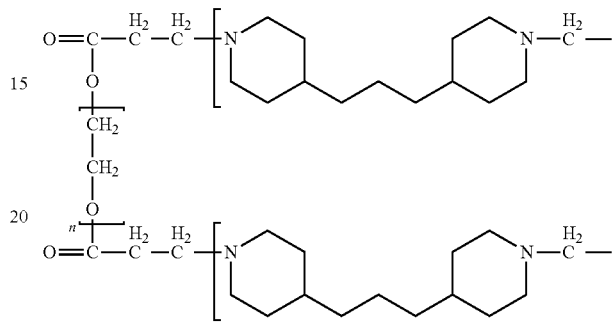

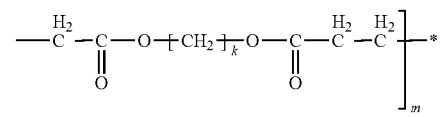

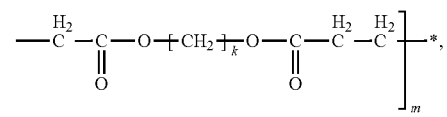

wherein k is a natural number ranging from 4 to 10, n is a natural number ranging from 11 to 45, and m is a natural number ranging from 10 to 100, wherein a molecular weight of the polyethylene glycol-based compound (A) is 500 to 8,000, wherein a molecular weight of the poly (β-amino ester)-based oligomer (B) is 1,000 to 5,000, wherein a molecular weight of the block copolymer is 3,000 to 32,000, wherein a molecular weight ratio of the polyethylene glycol-based compound (A) and the poly (β-amino ester)-based oligomer (B) is 1:1-4 wherein the block copolymer forms a hydrogel at pH 7.0 to 7.4 and a sol-state at pH 3.0 to under 7.0.

2. The pH- and temperature-sensitive block copolymer according to claim 1, wherein the molecular weight of the methoxy polyethylene glycol (MPEG) where R in the formula 1 represents methyl group is 1,000 to 7,000.

3. The pH- and temperature-sensitive block copolymer according to claim 1, which is represented by the following formula:

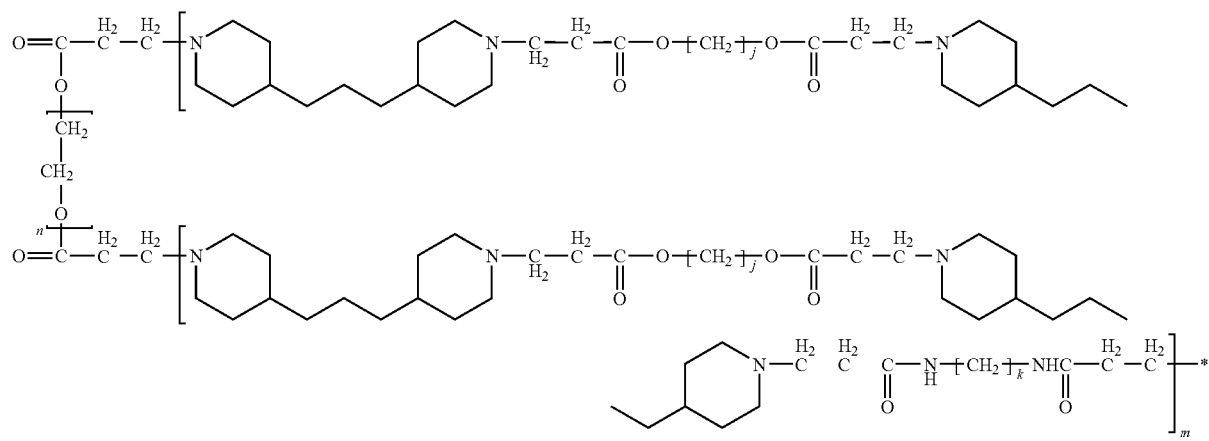

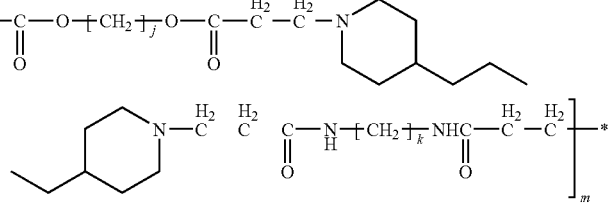

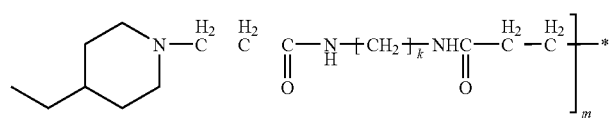

wherein j and k is a natural number ranging from 4 to 10, n is a natural number ranging from 11 to 45.

4. A hydrogel composition comprising a block copolymer according to claim 1.

5. A drug carrier comprising a block copolymer according to claim 1.

6. A drug carrier comprising:
a block copolymer according to claim 1; and bioactive materials included in the block copolymer.

7. The drug carrier according to claim 6, wherein the bioactive materials is protein such as insulin, symlin, exendin, somatokine, hGH, G-CSF, EPO, anti-cancer drug such as paclitaxal, chlorambucil, interferon, single chain Fv antibodies, monoclonal antibodies, vaccine, antimicrobial drug, steroid, anti-inflammatory drugs, sex hormone, immune retarder, antiviral drug, anesthetic, antiemetics, or antihistamine and further includes excipient, stabilization drug, conditioner, binder, or disintergrant,
wherein the compound further includes additive or solvent.

8. The drug carrier according to claim 6, wherein the drug carrier is an oral medication or non-oral medication and preferably vein, muscle, or hypodermic injection material.

* * * * *